(12) United States Patent
Dauphinais et al.

(10) Patent No.: US 11,676,047 B1
(45) Date of Patent: Jun. 13, 2023

(54) AIR QUALITY DATA SERVICING

(71) Applicant: 3M INNOVATIVE PROPERTIES COMPANY, St. Paul, MN (US)

(72) Inventors: Amanda B. Dauphinais, Eagan, MN (US); Justine S. Fritz, Woodbury, MN (US); Jessica B. Dugan, Minneapolis, MN (US); Brian L. Linzie, Stillwater, MN (US); Julian A. Politis, Hudson, WI (US); Nicolas A. Echeverri, Woodbury, MN (US); Rebecca L. Blakey, Hudson, WI (US); Patrick S. Hiner, Woodbury, MN (US); Andrew M. Boyd, Minneapolis, MN (US); Niya P. Johnson, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 591 days.

(21) Appl. No.: 16/663,923

(22) Filed: Oct. 25, 2019

Related U.S. Application Data

(60) Provisional application No. 62/771,426, filed on Nov. 26, 2018, provisional application No. 62/750,648, filed on Oct. 25, 2018.

(51) Int. Cl.
| | |
|---|---|
| *G06N 5/04* | (2006.01) |
| *G01N 33/00* | (2006.01) |
| *F24F 11/30* | (2018.01) |
| *G01N 1/22* | (2006.01) |
| *F24F 110/50* | (2018.01) |

(52) U.S. Cl.
CPC .............. *G06N 5/04* (2013.01); *F24F 11/30* (2018.01); *G01N 1/2273* (2013.01); *G01N 33/0075* (2013.01); *F24F 2110/50* (2018.01)

(58) Field of Classification Search
CPC ........ G06N 5/04; F24F 11/30; F24F 2110/50; G01N 1/2273; G01N 33/0075
See application file for complete search history.

(56) References Cited

U.S. PATENT DOCUMENTS

| | | | |
|---|---|---|---|
| 4,316,365 A | 2/1982 | Mueller et al. | |
| 5,001,463 A | 3/1991 | Hamburger | |
| 6,693,546 B2 * | 2/2004 | Skardon | G01N 33/0075 702/29 |
| 6,894,620 B2 | 5/2005 | Reinhardt et al. | |
| 6,993,414 B2 | 1/2006 | Shah | |
| 7,012,685 B1 | 3/2006 | Wilson | |
| 7,174,273 B2 | 2/2007 | Goldberg | |
| 7,244,294 B2 | 7/2007 | Kates | |
| 7,261,762 B2 | 8/2007 | Kang et al. | |
| 7,389,158 B2 * | 6/2008 | Desrochers | G01N 33/0034 700/277 |
| 8,029,608 B1 | 10/2011 | Breslin | |
| 8,613,792 B2 | 12/2013 | Ragland et al. | |
| 8,623,117 B2 | 1/2014 | Zavodny et al. | |
| 8,626,456 B2 | 1/2014 | Moore et al. | |
| 8,704,672 B2 | 4/2014 | Hoglund et al. | |
| 9,120,043 B2 | 9/2015 | Johansson et al. | |
| 9,200,995 B2 | 12/2015 | Ahola et al. | |
| 9,207,727 B2 | 12/2015 | Balogh et al. | |
| 9,481,004 B2 | 11/2016 | Vickers et al. | |
| 9,517,429 B2 | 12/2016 | Beier | |
| 9,552,715 B2 | 1/2017 | Breslin | |
| 9,593,861 B1 | 3/2017 | Burnett | |
| 9,857,301 B1 | 1/2018 | Nourbakhsh | |
| 2002/0104967 A1 | 8/2002 | Kouznetsov | |
| 2005/0150304 A1 | 7/2005 | Gustafson et al. | |
| 2005/0242201 A1 * | 11/2005 | Shorrock | F24F 11/30 236/49.3 |
| 2006/0100796 A1 | 5/2006 | Fraden et al. | |
| 2007/0013534 A1 | 1/2007 | DiMaggio | |
| 2008/0198896 A1 | 8/2008 | Nair | |
| 2009/0165644 A1 | 7/2009 | Campbell | |
| 2011/0185895 A1 | 8/2011 | Freen | |
| 2011/0253359 A1 * | 10/2011 | Stockton | F24F 11/30 165/250 |
| 2012/0318073 A1 | 12/2012 | Zavodny | |
| 2013/0260668 A1 * | 10/2013 | Stakutis | F24F 11/30 454/256 |
| 2014/0278681 A1 | 9/2014 | Cox et al. | |
| 2016/0174146 A1 | 6/2016 | Wang et al. | |
| 2016/0184755 A1 | 6/2016 | Chen et al. | |
| 2017/0038088 A1 * | 2/2017 | Korber | F24F 11/30 |
| 2017/0161646 A1 * | 6/2017 | Abuelsaad | G06F 16/29 |
| 2017/0189844 A1 | 7/2017 | McLeod et al. | |
| 2017/0320004 A1 | 11/2017 | Allegorico et al. | |
| 2017/0358022 A1 * | 12/2017 | Deak | G06Q 30/0631 |
| 2017/0361259 A1 | 12/2017 | Fox et al. | |
| 2018/0012479 A1 | 1/2018 | Seaton et al. | |
| 2021/0041124 A1 * | 2/2021 | Ajax | F24F 11/52 |

FOREIGN PATENT DOCUMENTS

| | | |
|---|---|---|
| WO | WO 2011-29574 | 3/2011 |
| WO | WO 2018-031406 | 2/2018 |
| WO | WO 2018-039231 | 3/2018 |

OTHER PUBLICATIONS

International Search Report, PCT/US2017/045508/, dated Oct. 18, 2017, 3 pages.

* cited by examiner

*Primary Examiner* — Tung S Lau
(74) *Attorney, Agent, or Firm* — Ann K. Gallagher

(57) ABSTRACT

The present disclosure provides systems and methods for collecting distributed information regarding air quality and air management system performance, and providing recommendations for affecting the air quality, the air management system, or individuals subject to or in control of either the air quality or the air management system.

2 Claims, No Drawings

AIR QUALITY DATA SERVICING

CROSS REFERENCE TO RELATED APPLICATIONS

This application claims the benefit of provisional Application No. 62/771,426, filed Nov. 26, 2018, and also claims the benefit of provisional Application No. 62/750,648, filed Oct. 25, 2018, the disclosure of which is incorporated by reference in its/their entirety herein.

BACKGROUND

Human progress and related modifications to the global environment have led to worsening quality of breathable air. Awareness of the issue is nascent, particularly in the United States, but is gradually increasing to the point where demand for solutions is beginning to grow. While several devices currently exist for monitoring pollution, indoor air quality, and personal respiration, such devices are likely discrete and localized. Data from such devices remains siloed, leading to incomplete or insufficiently realized prescriptions and recommendations.

SUMMARY

The present disclosure provides integrated systems and networks for maximizing the impact and viability of air quality data. Suitable devices (e.g., HVAC systems, filters, room air purifiers, and air quality monitors, personal breathing apparatuses) relating to air quality and operable according to the disclosure can be found, for example, in International Publication Nos. WO2018/031406 (Arthur et al.), WO 2018/039231 (Fox et al.), and U.S. Pat. No. 9,857,301 (Nourbakhsh et al.), each of which is incorporated by reference in its entirety herein.

In one aspect, the present disclosure provides one or more wirelessly connected, smart air filters in communication with a national network of millions of connected air filters and monitors. The network provides increased insight around filter and HVAC performance, consumer profiles and recurring behavior, and high-risk situations.

In another aspect, the present disclosure provides one or more connected air filters and monitors streaming live indoor air quality data from hyper-local spaces, providing a live dataset on room-level indoor air quality.

In another aspect, the present disclosure provides a single wirelessly connected, smart air filter in communication with a national network of millions of connected air filters and monitors. The network and related system provide increased insight around filter and HVAC performance, consumer profiles and recurring behavior, and high-risk situations. The network and system offer property insurers live, high fidelity filter life and HVAC performance information via its mobile application or device interface In another aspect, the present disclosure provides one or more wirelessly connected, smart air filters in communication with a national network of millions of connected air filters and monitors. The system includes a computer program that provides any hotelier/restaurateur with increased insight around their filter and HVAC performance, impacting indoor air quality, energy bills and preventing costly breakdowns.

In another aspect, the present disclosure provides HVAC maintenance teams insight over their customers' essential home systems, and ultimately provide recommendations to improve their ability to monitor filter and HVAC performance, conduct early diagnosis, enable auto-replenishment of filters, fix massive breakage before it occurs, and ensure better overall HVAC performance for their customers.

In another aspect, the present disclosure provides one or more connected, smart filters, which stream live data on filter and HVAC performance, with a series of air quality monitors located in a factory space, and an integrated mobile application that provides any health and safety manager with increased insight around their filter and HVAC performance, indoor, room-by-room, hyper-local air quality, and overall employee respiratory safety.

In another aspect, the present disclosure provides one or more wirelessly connected, smart air filters in communication with a national network of millions of connected air filters and monitors. A program drawing information from the network allows any real estate provider, underwriter, or marketplace to offer a better breathing solution for home owners, hosts, buyers, and renters, offering live, high fidelity filter life and HVAC performance information via its mobile application or device interface.

In another aspect, the present disclosure provides one or more wirelessly connected, smart air filters in communication with a national network of millions of connected air filters and monitors. The system includes a computer program that provides any smart home product user with increased insight around their filter and HVAC performance, impacting indoor air quality, energy bills and preventing costly breakdowns.

In another aspect, the present disclosure provides one or more connected, smart filters, which stream live data on filter and HVAC performance, with a series of air quality monitors, and an integrated mobile application or other computer program that allows health insurers to identify the outdoor air quality and the average indoor air quality across homes and neighborhoods. The platform then can leverage the data to provide insights that improve accuracy in underwriting of a customer's insurance plan.

In another aspect, the present disclosure provides one or more connected, smart filters, which stream live data on filter and HVAC performance, with a series of air quality monitors, and an integrated mobile application or other computer program that allows any healthcare product manufacturer to provide neighborhood level predictions of a location's indoor and outdoor air quality and provide recommendations to improve their user's air quality and ensure better breathing.

In yet another aspect, the present disclosure provides one or more connected, smart filters, which stream live data on filter and HVAC performance, with a series of air quality monitors, and an integrated mobile application or other computer program that allows any hotel, restaurant or customer-facing establishment to identify their outdoor air quality and the average indoor air quality across their neighborhood. The platform then can provide recommendations to improve air quality and ensure better breathing for its customers.

In yet another aspect, the present disclosure provides one or more connected, smart filters, which stream live data on filter and HVAC performance, with a series of air quality monitors at geographically linked locations, and an integrated mobile application or other computer program that provide insights that indicate the relative risk of insuring homes in a geographic area.

The words "preferred" and "preferably" refer to embodiments of the invention that may afford certain benefits, under certain circumstances. However, other embodiments may also be preferred, under the same or other circumstances.

Furthermore, the recitation of one or more preferred embodiments does not imply that other embodiments are not useful, and is not intended to exclude other embodiments from the scope of the invention.

As recited herein, all numbers should be considered modified by the term "about".

As used herein, "a", "an", "the", "at least one", and "one or more" are used interchangeably. Thus, for example, a core comprising "a" pattern of recesses can be interpreted as a core comprising "one or more" patterns.

Also herein, the recitations of numerical ranges by endpoints include all numbers subsumed within that range (e.g., 1 to 5 includes 1, 1.5, 2, 2.75, 3, 3.80, 4, 5, etc.).

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties). The term "substantially", unless otherwise specifically defined, means to a high degree of approximation (e.g., within +/−10% for quantifiable properties) but again without requiring absolute precision or a perfect match. Terms such as same, equal, uniform, constant, strictly, and the like, are understood to be within the usual tolerances or measuring error applicable to the particular circumstance rather than requiring absolute precision or a perfect match.

The above summary of the present disclosure is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exhaustive list.

DETAILED DESCRIPTION

Various embodiments and implementations will be described in detail. These embodiments should not be construed as limiting the scope of the present application in any manner, and changes and modifications may be made without departing from the spirit and scope of the inventions. Further, only some end uses have been discussed herein, but end uses not specifically described herein are included within the scope of the present application. As such, the scope of the present application should be determined by the claims.

The present inventors sought to make hyper-local Air Quality data and its environmental and health impacts accessible to every person and business, so that they can make informed decisions about their living and working environments. Air Quality, both indoor and outdoor, has dramatic impacts on a person's health, productivity and general wellness. By providing insight into someone's air quality and the right tools on how to improve that air quality, the system and methods of the present disclosure can ensure every person can breathe better, cleaner air.

HomeAQ

Room-by-room, hyper-local air quality, furnace performance and filter life data are key indicators of HVAC and furnace care. Through providing insight into indoor home air quality and the tools to improve it, we can ensure every property stakeholder is equipped to customize coverage and monitor compliance to prevent major maintenance issues or household accidents.

The Problem

In a world where data is increasingly accessible, more than ever, insurers are actively seeking information about the homes and neighborhoods where they're providing coverage. However, when it comes to processing claims, insurers have limited information on consumer behavior, maintenance negligence, and filter and HVAC usage that could be leading to appliance breakdowns and more costly damages.

The Solution

Our national network of millions of connected air filters and monitors stream live indoor air quality data from hundreds of thousands of homes, offices, restaurants and hotels across North America, providing the world's premier, constantly updating dataset on neighborhood-level indoor and outdoor air quality. By combining our connected, smart filter with our national network of millions of connected air filters and monitors, HomeAQ provides increased insight around filter and HVAC performance, consumer profiles and recurring behavior, and high-risk situations.

HomeAQ offers property and appliance insurers live, high fidelity HVAC performance, filter life and change frequency, air pressure and temperature data via its mobile application or device interface. Now key property stakeholders are able to ensure maintenance, usage and utility compliance, provide recommendations to improve air quality, and better differentiate their coverage.

Features:
1. Connected Air Filters and Air Quality Monitors—equip your customers with connected home products to manage environmental quality and utility; retro-fit existing appliances with smart sensors.
2. Embedded HVAC Insights—access live data on filter life and HVAC performance cycles.
3. Predictive Models—leveraging knowledge about customer location, nearby air quality and insights from an air quality engine (predictive or otherwise), receive updates on potential HVAC breakage before it happens to prevent costly replacements.
4. Engagement and Incentives—create opportunities to engage with users post-transaction, and incentivize them to take care of related property.
5. Auto-Reorder—insights into filter life enable auto-replenishment to prevent over-use and strain on HVAC appliances More than just air quality data, HomeAQ enables every appliance insurer to build further trust with customers and provide them insight to improve their home and wellness while more accurately underwriting policies to better ensure financial sustainability.

WorkAQ

The Problem

New workforce dynamics, trends like urbanization and the rise of entrepreneurship has dramatically altered workplace designs, with millions globally working in office spaces that are denser than ever before and are shared with a diverse set of other companies. In fact, average space per employee is decreasing from over 250 sq. ft./employee to less than 60 sq. ft. This new dense, shared office dynamic, combined with a heightened awareness of air quality and personal health, has led co-working spaces and dynamic office providers to explore new ways to align their workspace with health and wellness while building trust with their tenants. Currently, there is no low-cost way to gain insights into a space's air quality at scale and gain actionable insight to better manage these spaces to improve air quality and the overall tenant experience.

Additionally, studies have shown that an increase in air quality correlates with added productivity. In an environment where productivity and efficiency is a core value driver, ensuring a healthy work environment is a key potential differentiator.

The Solution

Our connected air filters and monitors stream live indoor air quality data from hyper-local spaces, providing a live dataset on room-level indoor air quality.

WorkAQ allows any coworking space to identify their specific indoor air quality—in both the shared space and in private offices—to accurately measure air quality and gain insights into the activity that is occurring within the space. The platform's machine learning engine can provide recommendations to improve your air quality and ensure better breathing for your customers, while providing high fidelity analytics into workspace usage, design and employee experience. When over-layed with additional datasets, an increase in air quality can directly correlate with increased productivity, generating clear ROI for major stakeholders.

Features:
1. Connected Air Filters and Monitors—equip co-working space with connected home products to manage environmental quality and utility.
2. AQ Predictor—leverage air quality data sets to gain live insight into the outdoor and indoor air quality in your co-working space.
3. Predictive Models—leveraging knowledge about customer location, nearby air quality and insights from an air quality engine (predictive or otherwise), receive updates on potential breakage before it happens to prevent costly replacements.
4. AQ Showcase—promote properties with superior air quality to customers to prove premium environment and alignment with health/wellness goals, including certification badge. Showcase your air quality against to other coworking spaces in the same region. Accessible via API and integrated into a website.
5. Recommendation Engine—leveraging knowledge about your location, nearby air quality and insights from an air quality engine (predictive or otherwise), users receive recommendations to ensure you maximize your indoor air quality and promote the best environment, design workspaces most efficiently, and optimize the use of WorkAQ products.
6. Engagement and Incentives—create opportunities to engage with users post-transaction, and incentivize them to take care of related property.

More than just air quality data, WorkAQ enables co-working spaces to build further trust with customers and prevent costly damage to the appliances core to operating their facilities.

HomeAQ II

Room-by-room, hyper-local air quality, furnace performance and filter life data are key indicators of HVAC and furnace care. Through providing insight into indoor home air quality and the tools to improve it, we can ensure every property stakeholder is equipped to customize coverage and monitor compliance to prevent major maintenance issues or household accidents.

The Problem

In a world where data is increasingly accessible, more than ever, insurers are actively seeking information about the homes and neighborhoods where they're providing coverage. However, when it comes to processing claims, insurers have limited information on consumer behavior and negligence that could be leading to appliance breakdowns and more costly damages.

The Solution

Our national network of millions of connected air filters and monitors stream live indoor air quality data from hundreds of thousands of homes, offices, restaurants and hotels across North America, providing the world's premier, constantly updating dataset on neighborhood-level indoor and outdoor air quality. By combining connected, smart filter with our national network of millions of connected air filters and monitors, HomeAQ provides increased insight around filter and HVAC performance, consumer profiles and recurring behavior, furnace usage and maintenance patterns, and high-risk situations.

HomeAQ offers property insurers live, high fidelity filter life and HVAC performance information via its mobile application or device interface. Now key property stakeholders are able to ensure maintenance, usage and utility compliance, provide recommendations to improve air quality, and better differentiate their coverage.

Features:
1. Connected Air Filters and Monitors—equip customers with connected home products to manage environmental quality and utility; retro-fit existing appliances with smart sensors.
2. Home and Consumer Profile—understand customers, their behaviors, and their home to better develop custom policies and recommendations.
3. AQ Predictor—leverage air quality data sets to gain live insight into the outdoor and indoor air quality in a household and neighborhood.
4. Embedded HVAC Insights—access live data on filter life and HVAC performance cycles.
5. Recommendation Engine—leveraging knowledge about a location, nearby air quality, and insights from an air quality engine (predictive or otherwise), you can provide improvement recommendations to help customers minimize their risk of household damage.
6. Engagement and Incentives—create opportunities to engage with users post-transaction and incentivize them to take care of related property.

More than just air quality data, HomeAQ enables every insurer to build further trust with customers and provide them insight to improve their home and wellness while more accurately underwriting policies to better ensure financial sustainability.

HospitalityAQ

The Problem

Today's hotel, restaurant and bar customers are increasingly aware of risks of poor air quality and a growing health and wellness culture is creating new expectations around the indoor environment. Even more importantly, over 30 million Americans have respiratory conditions such as asthma and COPD and a growing population actively seek information about the air quality in hotels where they stay or restaurants they visit.

However, the vast majority of today's hotels, restaurants and bars provide no insight into their establishments' outdoor or indoor air quality, leaving consumers uninformed and ill-equipped to optimize their air quality.

The Solution

By combining our connected, smart filter, which streams live data on filter and HVAC performance, with our national network of millions of connected air filters and monitors, an integration with HospitalityAQ provides any hotelier/restaurateur with increased insight around their filter and HVAC performance, impacting indoor air quality, energy bills and preventing costly breakdowns.

With a simple integration, HospitalityAQ allows any hospitality establishment to offer live, high fidelity filter life and HVAC performance information via its mobile application or device interface. Give your customers trust and control over their indoor environment, and ultimately provide recommendations to improve the users' air quality and ensure a higher quality experience for customers looking for rest and relaxation.

Features:
1. Connected Air Filters and Monitors—equip a space with connected products to manage environmental quality and utility.
2. Embedded HVAC Insights—access live data on filter life and HVAC performance, to better maintain properties, lower energy bills and improve indoor air quality.
3. Embedded AQ—leverage air quality data to provide live insight into the outdoor and indoor air quality in a property's region.
4. Predictive Models—leveraging knowledge about property location, nearby air quality and insights from an air quality engine (predictive or otherwise), receive updates on potential breakage before it happens to prevent costly replacements.
5. Recommendation Engine—leveraging knowledge about your location, nearby air quality and insights from an air quality engine (predictive or otherwise), users receive recommendations to ensure you maximize your indoor air quality and promote the best environment, design facilities most efficiently, and optimize the use of HospitalityAQ products.
6. Consumer Profile—understand your customer, their behaviors, and their smart home preferences to ensure a personalized user experience with custom temperature and humidity controls, and even room-specific scents.

More than just air quality data, HospitalityAQ enables every hotel, bar or restaurant to build further trust with customers and provide them better breathing wellness and a personalized experience every time.

HomeAQ Platform

Hyper-local air quality, furnace performance and filter life data are key indicators of HVAC performance. Through providing insight into indoor home air quality and the tools to improve it, we can ensure every HVAC professional has the information they need on filter quality, life, type, installation and replacement specs, and is equipped to deliver top-tier service and ensure every customer has a life of better breathing.

The Problem

HVAC maintenance professionals are facing increasing expectations given today's seamless access to information and data. At the same time, home owners often neglect basic furnace maintenance, and forget to call the Pros, leading to broken equipment and distrust in the systems. HVAC Pros currently have no way of ensuring the filter is being changed, tracking furnace performance, or engaging the home owner to perform yearly maintenance before to avoid equipment failure.

While consumers are increasingly aware of risks of poor air quality and a growing health and wellness culture is creating new expectations around the indoor environment, they are just as increasingly negligent and uninformed about their HVAC and filter stability. Consumers are left uninformed and ill-equipped to optimize their air quality, and HVAC maintenance companies being run in a fundamentally reactive way.

The Solution

By combining our connected, smart filter, which streams live data on pressure and temperature, filter life, and HVAC performance, with our national network of millions of connected air filters and monitors, an integration with HomeAQ provides any HVAC maintenance pro with increased insight around a customer's filter and HVAC performance, improving their ability to prevent major performance issues, accurately triage on-premise visits, and reliably predict inventory and revenue.

With a simple integration, HomeAQ allows any HVAC product to offer live, high quality filter life and HVAC performance information via its mobile application or device interface. Give your maintenance teams insight over their customers' essential home systems, and ultimately provide recommendations to improve their ability to monitor filter and HVAC performance, conduct early diagnosis, enable auto-replenishment of filters, fix massive breakage before it occurs, and ensure better overall HVAC performance for their customers.

Features:
1. Embedded HVAC Insights—access live data on filter life and HVAC performance, helping users better maintain their home, lower energy bills and improve indoor air quality.
2. Embedded AQ—leverage air quality data to provide live insight into the outdoor and indoor air quality in a user's neighborhood.
3. Home and Consumer Profile—understand customers, their behaviors, their filter change compliance, and their home to better serve them in the field.
4. Predictive Maintenance Engine—leveraging knowledge about a user's home, HVAC data and filter performance and nearby air quality, an AI engine (predictive or otherwise) can provider users notifications and recommendations to check filter live and HVAC stability, decrease electricity spend and prevent costly HVAC breakdowns.
5. Auto-Reorder—insights into filter life enable auto-replenishment direct to consumer or through delivery by HVAC company to prevent over-use and strain on HVAC appliances.
6. Engagement and Communication—easily communicate with customers via our chat service; schedule times, provide updates, and answer post-visit follow up questions.
7. Service Efficiency—utilize air quality and consumer data to effectively optimize service routes, manage inventory, dispatch specialized pros, and manage customer expectations.

More than just air quality data, HomeAQ enables every HVAC maintenance company to build further trust with customers and provide them insight to improve their home and wellness.

FactoryAQ Platform

The Problem

Today's workforce is increasingly aware of the air quality of their workplace, and a growing health and wellness culture is creating new expectations around indoor environments. As a result, factories and other industrial settings have new expectations of raising the bar on safety standards, implementing programs to improve workforce satisfaction and safety, and ensuring that the environments their employees are exposed to are appropriately monitored and quality-controlled.

The Solution

By combining our connected, smart filter, which streams live data on filter and HVAC performance, with a series of our air quality monitors located in the factory space, an integration with FactoryAQ provides any health and safety manager with increased insight around their filter and HVAC performance, indoor, room-by-room, hyper-local air quality, and overall employee respiratory safety.

Employees want to know that the air they are breathing is not negatively impacting their health, their employer is making a dedicated effort to ensure it remains clean, and filtered at a high-quality. Offering proven air quality, and elevated standards of health and safety will help businesses differentiate themselves from the noise in a tight labor market.

It's also proven that better breathing results in higher productivity and employee output. Our AQ API can integrate with your workforce analytics tool to correlate employee productivity to real-time air quality, enabling leadership to make smart decisions as it relates to environmental quality and employee retention.

Features:
1. Connected Air Filters and Monitors—equip customers with connected home products to manage environmental quality and utility; retro-fit existing appliances with smart sensors
2. Embedded HVAC Insights—access continually updated data on filter life and HVAC performance cycles
3. Predictive Models—leveraging knowledge about customer location, nearby air quality and insights from an air quality engine (predictive or otherwise), receive updates on potential breakage before it happens to prevent costly replacements
4. Embedded AQ—leverage air quality data to provide live insight into the outdoor and indoor air quality in a users' neighborhood.
5. Notifications and Recommendation Engine—leveraging knowledge about a user's home, HVAC data and filter performance and nearby air quality, an AI engine (predictive or otherwise) can provide users notifications and recommendations to improve air quality, decrease electricity spend and prevent costly HVAC breakdowns.
6. Productivity Analysis—correlate air quality metrics with employee output, and make AQ improvements to increase productivity and employee motivation More than just air quality data, FactoryAQ enables every health and safety professional to build further trust with employees and provide them a best-in-class work environment.

HomeAQ III
The Problem

Today's consumers are becoming more aware of the health risks associated with bad air quality, and a growing health and wellness culture is creating new expectations around the indoor environment. Over 30 million Americans have respiratory conditions such as asthma and COPD and a growing population actively seek information about the air quality of homes they're planning to visit or purchase. At the same time, companies representing, and often investing in, these properties have little insight into their overall management and environmental quality.

The Solution

Our national network of millions of connected air filters and monitors stream live indoor air quality data from hundreds of thousands of homes, offices, restaurants and hotels across North America, providing the world's premier, constantly updating dataset on neighborhood-level indoor and outdoor air quality. By combining our connected, smart filter with our national network of millions of connected air filters and monitors, HomeAQ provides increased insight around filter and HVAC performance, impacts on indoor air quality and energy bills, and can prevent costly breakdowns.

HomeAQ allows any real estate provider, underwriter, or marketplace to offer a better breathing solution for home owners, hosts, buyers, and renters, offering live, high fidelity filter life and HVAC performance information via its mobile application or device interface. Now key property stakeholders are able to ensure maintenance, usage and utility compliance, provide recommendations to improve air quality, and better differentiate their properties.

Features:
1. Connected Air Filters and Monitors—equip your customers with connected home products to manage environmental quality and utility.
2. Embedded HVAC Insights—access live data on filter life and HVAC performance, helping users better maintain their home, lower energy bills and improve indoor air quality.
3. Air Quality Assurance—leverage air quality data sets to gain live insight into the indoor air quality of your properties.
4. AQ Showcase—promote properties with superior air quality to customers to prove premium environment and alignment with health/wellness goals. Showcase your air quality against to other areas of the city, country or national averages. Accessible via API and integrated into your online booking platform.
5. Recommendation Engine—leveraging knowledge about your location, nearby air quality and insights from an air quality engine (predictive or otherwise), users receive recommendations to ensure you maximize your indoor air quality and promote the best environment.
6. Engagement and Incentives—create opportunities to engage with your users post-transaction, and incentivize them to take care of your property.

More than just air quality data, HomeAQ enables every smart home company to build further trust with customers and provide them insight to improve their home and wellness.

HomeAQ Platform II
The Problem

Today's smart home customers have increasing expectations of seamless integration and connected home devices that provide insight into a broad array of subjects in the home and beyond. At the same time, consumers are increasingly aware of risks of poor air quality and a growing health and wellness culture is creating new expectations around the indoor environment. Even more importantly, over 30 million Americans have respiratory conditions such as asthma and COPD and a growing population actively seek information about the air quality in hotels where they stay or restaurants they visit.

However, the vast majority of today's connected home devices provide no insight into a users' outdoor or indoor air quality, leaving consumers uninformed and ill-equipped to optimize their air quality.

The Solution

By combining our connected, smart filter, which streams live data on filter and HVAC performance, with our national network of millions of connected air filters and monitors, an integration with HomeAQ provides any smart home product user with increased insight around their filter and HVAC performance, impacting indoor air quality, energy bills and preventing costly breakdowns.

With a simple integration, HomeAQ allows any connected product to offer live, high fidelity filter life and HVAC performance information via its mobile application or device interface. Give your users trust and control over their indoor environment and essential home systems, and ultimately provide recommendations to improve the users' air quality and ensure better home maintenance.

Features:
1. Embedded HVAC Insights—access live data on filter life and HVAC performance, helping users better maintain their home, lower energy bills and improve indoor air quality.
2. Embedded AQ—leverage air quality data to provide live insight into the outdoor and indoor air quality in a users' neighborhood.
3. Notifications and Recommendation Engine—leveraging knowledge about a user's home, HVAC data and filter performance and nearby air quality, an AI engine (predictive or otherwise) can provider users notifications and recommendations to improve air quality, decrease electricity spend, prevent costly HVAC breakdowns, and autonomously connect with other air quality related solutions to provide a holistic air quality management for the home (i.e., purifiers, thermostats, smart vents, etc.).
4. Easy Integration—embed air quality information into a mobile application or other computer program with just a few lines of code.
5. Co-created Experience—co-branding and co-development of user experience to best engage customers around smart home products and air quality.
6. New Revenue Opportunities—leverage our insights to elevate customers to premium software upgrades or cross-sell additional products and services.

More than just air quality data, HomeAQ enables every smart home company to build further trust with customers and provide them insight to improve their home and wellness.

AQGenie I

The Problem

With over 30 million Americans diagnosed with respiratory conditions such as asthma and COPD, today's health insurers are aware of the health risks of bad air quality. More than ever, insurers are actively seeking information about the air quality in houses and neighborhoods where their customers live.

The Solution

Our national network of millions of connected air filters and monitors stream live indoor air quality data from hundreds of thousands of homes across North America, providing the world's premier constantly updating dataset on neighborhood-level indoor and outdoor air quality.

AQGenie allows health insurers to identify the outdoor air quality and the average indoor air quality across homes and neighborhoods. The platform then can leverage the data to provide insights that improve accuracy in underwriting of a customer's insurance plan.

Features:
1. AQ Predictor—leverage air quality data sets to gain live insight into the outdoor and indoor air quality in a household or neighborhood.
2. Recommendation Engine—leveraging knowledge about a location, nearby air quality, and insights from an air quality engine (predictive or otherwise), you can provide improvement recommendations to help customers minimize their health risk from air quality.
3. Consumer Identification—with access to both outdoor and average indoor air quality data, you can better identify the health profile of prospective and current customers living in a given neighborhood.

AQapi

The Problem

The major health effects of poor outdoor and indoor air quality are well known. Over 30 million Americans have respiratory conditions such as asthma and COPD and an even larger population find themselves with compromised health where respiratory distress would create serious complications. However, the vast majority of people have no insight into their outdoor or indoor air quality, leaving them uninformed and vulnerable to environments that exacerbate respiratory conditions.

The Solution

Our national network of millions of connected air filters and monitors stream live indoor air quality data from hundreds of thousands of homes, offices and commercial establishments across North America, providing the world's premier live dataset on neighborhood-level indoor and outdoor air quality.

AQapi allows any connected product to offer live, accurate air quality information via its mobile application or device interface. With a simple call to AQapi, any healthcare product manufacturer can provide neighborhood level predictions of a location's indoor and outdoor air quality and provide recommendations to improve their user's air quality and ensure better breathing. Generate meaningful information for your customers and enable them to collect live, on-going data on their patients' environment.

Features:
1. Embedded AQ—leverage air quality data sets to provide live insight into the outdoor and indoor air quality for a targeted location's surrounding area.
2. Recommendation Engine—leveraging knowledge about a location, nearby air quality and insights from an air quality predictive engine, you can provide recommendations to your users on how to optimize indoor air quality.
3. Easy Integration—embed air quality information into a mobile application or other computer program with just a few lines of code.
4. Simple, Transparent Pricing—The API is self-serve and is easy to test without ever entering a credit card. Once you're ready, upgrade to the API plan that fits your needs.

More than just air quality data, AQapi enables every healthcare product to build further trust with customers and provide them insight to improve their environment and wellness.

AQGenie II

The Problem

Today's customers of hotels, restaurants, and bars are aware of the health risks of bad air quality and a growing health and wellness culture is creating new expectations around the indoor environment. Even more importantly, over 30 million Americans have respiratory conditions such as asthma and COPD and a growing population actively seek information about the air quality in hotels where they stay or restaurants they visit.

The Solution

Our national network of millions of connected air filters and monitors stream live indoor air quality data from hundreds of thousands of homes, offices, restaurants and hotels across North America, providing the world's premier constantly updating dataset on neighborhood-level indoor and outdoor air quality.

AQGenie allows any hotel, restaurant or customer-facing establishment to identify their outdoor air quality and the average indoor air quality across their neighborhood. The platform then can provide recommendations to improve your air quality and ensure better breathing for its customers.

Features:
1. AQ Predictor—leverage air quality data sets to gain live insight into the outdoor and indoor air quality in a given neighborhood.
2. AQ Showcase—promote properties with superior air quality to customers to prove premium environment and alignment with health/wellness goals. Showcase air quality against other areas of the city, country or national averages. Accessible via API and integrated into an online booking platform.
3. Better Breathing Recommendations—leveraging knowledge about location, nearby air quality and insights from an air quality predictive engine, users receive recommendations to ensure you maximize your indoor air quality and promote the best environment.

AQGenie III

The Problem

Today's home insurers are aware of the rising problem of poor air quality. Indoor smoking and unmaintained HVAC systems can pose a fire risk to home owners and the surrounding neighborhood.

Poor air quality can indicate if there is an irregularity with a device or appliance, indicating negligence or direct non-compliance. In a world where data is increasingly accessible, more than ever, insurers are actively seeking information about the conditions and environments of the homes and neighborhoods in their insurance portfolios. However, when it comes to processing claims, home insurers have limited insight into homeowners' potential habitual negligent behavior. Such behavior could overtime lead to appliance breakdowns or in some cases, more costly home damage.

The Solution

Our national network of millions of in home connected Air Filters and Air Quality monitors stream live indoor air quality data from hundreds of thousands of homes across North America, providing the world's premier constantly updating dataset on neighborhood-level indoor and outdoor air quality.

AQGenie allows insurers to identify the outdoor air quality and the average indoor air quality across homes and neighborhoods. By leveraging both air quality and prior HVAC maintenance data, the platform then can provide insights that indicate the relative risk of insuring homes in a geographic area.

Features:
1. AQ Predictor—leverage air quality data sets to gain live insight into the outdoor and indoor air quality in a household and neighborhood.
2. Better Breathing Recommendations—leveraging knowledge about a location, nearby air quality, and insights from an air quality algorithm and/or predictive engine, one can provide alerts and recommendations to help customers minimize their risk of home damage. Provide tips and status reports of neighborhood air quality to differentiate from competitive insurers and maintain a constant touchpoint to engage with customers.
3. Consumer Identification—with access to both outdoor and average indoor air quality data, one can better identify the home and maintenance profile of prospective and current customers living in a given neighborhood.
4. Alerts, Tips and status reports for homeowners—as part of the insurance package—ability to differentiate from other insurance with these additional features.

More than just air quality data, AQgenie enables every insurer to build further trust with customers and provide them insight to improve their home and wellness while more accurately underwriting policies to better ensure financial sustainability.

HomeAQ IV

The Problem

We live in a world where data is increasingly accessible, but when it comes to processing claims, property and appliance insurers still have limited information on consumer behavior as it pertains to preventative maintenance. More than ever, appliance insurance providers are actively seeking information about the homes and neighborhoods in their portfolios. Poor indoor air quality can be indicative of irregularity with a device or appliance, indicating negligence or direct non-compliance. For example, infrequent filter changes and irregularities with the HVAC system can predict costly appliance breakdowns before they happen.

The Solution

HomeAQ enables every appliance insurer to build trust with its customers around a shared goal —prevention of costly appliance failures. Homeowners are given the ability to improve their indoor air quality, while the insurer can utilize generated insights to more accurately underwrite policies and ensure financial sustainability. HomeAQ offers property and appliance insurers live, high fidelity HVAC performance, filter life and change frequency, air pressure and temperature data via its mobile application or device interface. Insurers can differentiate policy offerings and de-risk their portfolios by ensuring timely maintenance and proper usage compliance (e.g., frequent filter changes).

Features:
1. Connected Air Filters and Air Quality Monitors—Equip customers with connected air products to manage indoor air quality, as well as monitor HVAC system functionality.
2. Embedded HVAC Insights and auto-reorder—Access HVAC performance, air filter life and change frequency, air pressure and temperature data. Enable air filter auto-replenishment to prevent over-use and strain on HVAC appliances and avoid costly breakdowns.
3. Predictive Models—Receive updates on potential HVAC breakdowns before they happen to prevent costly replacements. Utilize national data pools to build client profiles, identify recurring high-risk behavior and address issues promptly.
4. Consumer Identification—With access to both outdoor and indoor air quality data, one can develop home and neighborhood profiles for potential customers.

HomeAQ V

The Problem

We live in a world where data is increasingly accessible, but when it comes to processing claims, property insurers still have limited information on consumer behavior. More than ever, insurance providers are actively seeking information about the homes and neighborhoods covered in their portfolios. When it comes to processing claims, insurers have limited information on consumer behavior and negligence that could be leading to costly home damages.

The Solution

HomeAQ enables every home insurer to build trust with its customers around a shared goal—prevention of costly home damage. Homeowners are given the ability to improve their indoor air quality, while the insurer can utilize generated insights to more accurately underwrite policies and ensure financial sustainability. HomeAQ offers property and appliance insurers live, high fidelity indoor air quality data via its mobile application or device interface. Insurers can differentiate policy offerings and de-risk their portfolios by ensuring timely response and homeowner policy terms compliance (e.g., non-smoking home).

Features:
1. Connected Air Filters and Air Quality Monitors—Equip customers with connected air products to manage indoor air quality.
2. Home and Consumer Profilers—Understand customers, their behaviors, and their home to develop custom policies and recommendations.
3. AQ Predictor—Leverage air quality data sets to gain live insight into the outdoor and indoor air quality of a household or neighborhood.
4. Recommendation Engine—Knowledge about a location's indoor and outdoor air quality and insights from an air quality predictive engine would allow sharing of timely alerts with customers to minimize the risk of home damage.
5. Engagement and Incentives—Create opportunities to engage with customers post transaction and incentivize them to take care of the property they have insured.
6. Consumer Identification—With access to both outdoor and indoor air quality data, one can develop home and neighborhood profiles for potential customers.

HVAC Platform

The Problem

Consumers are becoming aware of the health risks associated with poor indoor air quality but continue to be negligent about their HVAC system health. Homeowners often neglect basic furnace maintenance and forget to call professionals, leading to broken equipment and distrust in the system. Despite facing increasing expectations given today's seamless access to information and data, HVAC Pros still do not have a way of ensuring air filters are being changed on time and the furnace is running as expected. HVAC visits often are reactive responses to specific problems, instead of proactive maintenance.

The Solution

HVAC Platform products offer high fidelity HVAC performance, filter life and change frequency, air pressure and temperature data via its mobile application or device interface. The insights generated from the platform's data give HVAC professionals potential diagnostic information about their customers' home systems. This allows these professionals to proactively monitor HVAC system performance and provide timely recommendations for servicing. Such proactive diagnostics work improves their ability to prevent major performance issues and expensive malfunctions, accurately triage on-premise visits, and reliably predict parts inventory and revenue.

Features:
1. Embedded HVAC Insights—Access filter type, life and change frequency, air pressure and temperature data for timely HVAC system diagnostics.
2. Home and Consumer Profile—Understand customers, their behaviors, their filter change compliance, and their home to better serve them in the field.
3. Predictive Maintenance Engine—Leveraging users' home insights generated from HVAC Platform (e.g., HVAC system and filter performance), a predictive AI engine provides homeowners with notifications and recommendations regarding their HVAC system health.
4. Auto-Reorder—Insights into filter life enable direct-to-consumer auto-replenishment or delivery by an HVAC professional to prevent over-use and strain on HVAC appliances.
5. Engagement and Communication—Easily communicate with your customers via chat service; schedule times, provide updates, and answer post-visit follow up questions.
6. Service Efficiency—Utilize air quality and consumer data to effectively optimize service routes, manage inventory, dispatch specialized pros, and manage customer expectations.

HomeAQ Platform III

The Problem

Today's smart home customers have increasing expectations of seamless integration and connected home devices that provide insight into a broad array of subjects in their home and beyond. Consumers are increasingly aware of risks of poor indoor and outdoor air quality, and at the same time a growing health and wellness culture is creating new expectations around clean indoor air. However, certain of today's connected home devices provide little actionable insight into individual outdoor or indoor air quality, leaving them uninformed and ill-equipped to respond to poor air quality.

The Solution

With a simple integration, HomeAQ Platform allows any connected product to offer live, high-fidelity filter life, indoor air quality, and HVAC performance information via its mobile application or device interface. This provides any smart home product user with increased insight to help them improve their indoor air quality, lower their energy bills and prevent costly breakdowns of their furnace. HomeAQ Platform enables every smart home company to build further trust with customers by providing them with recommendations on how to improve their indoor air quality, as well as maintain their home HVAC systems.

Features:
1. Embedded HVAC Insights—Access air filter type, life and change frequency, air pressure and temperature data for timely HVAC system diagnostics.
2. Embedded AQ—Leverage air quality data to provide live insight into the outdoor and indoor air quality of user's environment (outside and at home).
3. Notifications and Recommendation Engine—Leveraging users' home insights generated from HomeAQ Platform, an AI engine (predictive or otherwise) provides homeowners with notifications and recommendations regarding their HVAC system health, air filter performance and overall indoor air quality.
4. Easy Integration—Embed air quality information into a given intelligent device mobile application or other computer program with just a few lines of code and autonomously connect with other air quality related solutions to provide a holistic home air quality management solution (including room air purifiers, thermostats, smart vents, fans, etc.).
5. Co-created Experience—potential for co-branding and co-development of user experience to best engage customers around smart home products and air quality.
6. New Revenue Opportunities—Leverage insights to elevate customers to premium software upgrades or cross-sell additional products and services.

WorkAQ II
The Problem

New workforce dynamics and trends (e.g., urbanization, increased entrepreneurship) have altered workplace design globally. Millions of individuals are working in office spaces that are denser than ever before and shared with a diverse set of companies. Average space per employee has decreased from over 250 sq. ft./employee to less than 60 sq. ft. This densely shared office dynamic, combined with heightened awareness of the link between poor indoor air quality and compromised health, has led co-working spaces providers to start exploring ways to align workspace with health and wellness. Currently, there is no low-cost way to gain insights into spaces indoor air quality at scale and gain actionable insight to improve indoor air quality at scale and overall tenant experience.

The Solution

WorkAQ allows any coworking space administrator to accurately measure indoor air quality and draw insights around activity happening in these spaces—both in shared spaces and in private offices. Our connected air filters and air quality monitors stream live indoor air quality data from hyper-local spaces, providing a dataset on room-level indoor air quality. The platform's machine learning engine can provide recommendations to improve indoor air quality and ensure occupants can breather better, cleaner air. It also provides high-fidelity analytics into workspace usage, design and employee experience. When over laid with additional datasets, an increase in air quality can directly correlate with increased productivity, generating clear ROI for major stakeholders. In an environment where productivity and efficiency are a core value driver, ensuring a healthy work environment is a key potential differentiator.

Features:
1. Connected Air Filters and Air Quality Monitors—Equip a co-working space with connected air quality related products to manage the tenants' environment. Showcase air quality against other co-working spaces in the same region. Accessible via API and integrated into one or more websites for presentation.
2. AQ Predictor—Leverage air quality data sets to gain live insight into the outdoor and indoor air quality in co-working spaces
3. Predictive Models—Leveraging knowledge about customer location, nearby air quality and insights from air quality predictive engine, receive updates on potential system (HVAC, air purifier, etc.) breakage before it happens to prevent costly replacements.
4. AQ Showcase—Promote co-working spaces with superior indoor air quality, connect with premium working environment and alignment with health/wellness goals
5. Recommendation Engine—Knowledge about a location's indoor and outdoor air quality and insights from any air quality engine would allow you maximize your indoor air quality, promote a healthier co-working environment, and design workspaces more efficiently
6. Engagement & Incentives—Create opportunities to engage with tenants post-transaction and incentivize them to take care of the relevant property.

HospitalityAQ II
The Problem

Today's hotel, restaurant and event space customers are increasingly aware of the risks of poor indoor air quality. A growing health and wellness culture is creating new expectations for real estate providers to offer superior indoor air quality environments. More than 30 million Americans have respiratory conditions such as asthma and COPD, and a growing population actively seeks information about the air quality in hotels where they stay or restaurants they visit. However, the vast majority of today's hotels, restaurants and bars provide no insight into their establishments' outdoor or indoor air quality, leaving consumers uninformed and ill-equipped to optimize their air quality.

The Solution

By combining our connected smart air filter, which streams live data on air filter and HVAC performance, with our national network of connected air filters and monitors, HospitalityAQ provides any hotelier/restaurateur with increased insight around their HVAC performance, indoor air quality, and energy use—which can save money and prevent costly breakdowns. With a simple integration, HospitalityAQ allows any hospitality establishment to receive high fidelity air filter and HVAC performance information via its mobile application or device interface. Give your customers trust and control over their indoor environment, and ultimately provide recommendations to improve the users' air quality and ensure a higher quality experience for customers looking for rest and relaxation.

Features:
1. Connected Air Filters and Air Quality Monitors—Equip a space with connected products to manage environmental quality and utility.
2. Embedded HVAC Insights—Access live data on filter life and HVAC performance, to better maintain properties, lower energy bills and improve indoor air quality.
3. Embedded AQ—Leverage air quality data to provide live insight into the outdoor and indoor air quality in a property's region.
4. Predictive Models—Leveraging knowledge about property location, nearby air quality and insights from an air quality engine (predictive or otherwise), receive updates on potential breakage before it happens to prevent costly replacements.
5. Recommendation Engine—Knowledge about a location's indoor and outdoor air quality and insights from an air quality engine (predictive or otherwise) would allow maximization of one's indoor air quality, promote a healthier environment for guests, and design facility spaces more efficiently.
6. Consumer Profile—Understand your customer, their behaviors, and their smart home preferences to ensure a personalized user experience with custom temperature and humidity controls, and even room-specific scents.

AQGenie IV
The Problem

Home buyers and renters are becoming increasingly aware of the health risks of bad air quality, and a growing health and wellness culture is creating new expectations around the indoor environment. More importantly, more than 30 million Americans have respiratory conditions such as asthma and COPD and this population actively seeks information about the air quality in homes they rent, buy, or visit. When purchasing a home or renting a place, it is challenging to know the history of the home and relative air quality safety.

The Solution

Our national network of connected air filters and monitors stream live indoor air quality data from hundreds of thousands of homes across North America, providing the world's premier, continuously updated data set on neighborhood- and home-level indoor and outdoor air quality. AQGenie allows real estate marketplaces to identify and display the outdoor air quality and the average indoor air quality across listed homes and neighborhoods. The platform also provides recommendations to improve the air quality in the properties listed to ensure better breathing for its customers.

Features:
1. 3rd Party Certification—Obtain certification for Air Quality, equivalent to the Energy Star™ for energy efficient appliances.
2. AQ Predictor—Leverage air quality data sets to gain live insight into the outdoor and indoor air quality in a neighborhood or neighborhoods of potential interest.
3, AQ Showcase—Promote properties with superior air quality to customers to prove premium environment and alignment with health/wellness goals. Showcase air quality of a given location or locations against other areas of the city, country or national averages. Accessible via API and integrated into an online booking platform.
4. Recommendation Engine—leveraging knowledge about a location, nearby air quality and insights from an air quality engine (predictive or otherwise), user receive recommendations on optimizing indoor air quality and promoting the best environment.

Home & Work AQ

The Problem

With more than 30 million Americans diagnosed with respiratory conditions such as asthma and COPD, today's health insurers are aware of the health risks of bad air quality. More than ever, insurers are actively seeking information about the air quality in houses and neighborhoods where their customers live. For customers with respiratory conditions, air quality data combined with insights around increased use of a rescue inhaler, prescription compliance, and strained breathing as a precursor to exacerbation will provide a comprehensive picture of a patient's environmental triggers and potential non-compliance.

The Solution

A vast national network of connected air filters and air quality monitors stream live indoor air quality data from hundreds of thousands of homes, offices, restaurants and hotels across North America, providing the world's premier, continuously updated dataset on neighborhood-level indoor and outdoor air quality.

This provides increased insight around at-home air quality, consumer profiles and behavior, and high-risk situations. Home & Work AQ offers health insurers live, high-fidelity air quality information via its mobile application or device interface. Now key insurance stakeholders can ensure health compliance, provide recommendations to improve air quality, and enhance accuracy in underwriting of a customer's insurance plan. More than just air quality data, Home & Work AQ empowers every health insurer to build further trust with customers and provide them insight to improve their health and wellness, while more accurately identifying high-risk consumers and underwriting policies to better ensure financial sustainability.

Features:
1. Connected Air Filters and Air Quality Monitors—Equip customers with connected home products to manage environmental quality and utility.
2. Home and Consumer Profiles—Understand customers, their behaviors, and their home to better develop custom policies and recommendations (are they compliant with their medication, are they non-smokers, are they changing their filters on time, do they own pets, etc.).
3. Better Breathing Recommendations—Leveraging knowledge about a location, nearby air quality, and insights from our leading air quality engine, one can provide recommendations to help customers minimize their risk of respiratory exacerbation.
4. Predictive Models—Leveraging knowledge about customer location, nearby air quality and insights from an air quality algorithm (predictive or otherwise), receive updates on user medication and non-smoking compliance to prevent respiratory triggers and hospital or clinic visits before they happen.
5. Engagement and Incentives—Create opportunities to engage with users post-on-boarding and incentivize them to take care of their environment and overall health.

AQapi II

The Problem

Consumers are becoming increasingly aware of the health risks of bad air quality, and a growing health and wellness culture is creating new expectations around the indoor environment. More importantly, more than 30 million Americans have respiratory conditions such as asthma and COPD and this population actively seeks information about the air quality in the homes they visit, rent, or live in.

At the same time, smart home users expect their home devices to seamlessly integrate with each other and provide insight into a broad array of health-related topics inside and outside the home. However, few connected home devices provide insight into users' outdoor or indoor air quality, leaving consumers uninformed and ill-equipped to optimize their air quality.

The Solution

A national network of connected air filters and monitors stream live indoor air quality data from hundreds of thousands of homes across North America, providing the world's premier, continuously updated dataset on neighborhood- and home-level indoor and outdoor air quality. AQapi allows any connected product to offer live, accurate air quality information via its mobile application or device interface. With a simple call to AQapi, devices can provide predictions about a user's indoor and outdoor air quality as well as recommendations to improve the air quality and ensure better breathing.

Features:
1. Embedded AQ—Leverage air quality data sets to provide live insight into the outdoor and indoor air quality for a targeted location's surrounding area.
2. Recommendation Engine—Leveraging knowledge about a location, nearby air quality and insights from an air quality predictive engine, one can provide recommendations to users on how to optimize indoor air quality.
3. Easy Integration—Embed air quality information into a mobile application or other computer program with just a few lines of code.
4. Simple, Transparent Pricing—The API is self-serve and is easy to test without ever entering a credit card. Once ready, an upgrade to the API plan is available that fits a variety of needs.

5. Better Breaking Recommendations—Through an AQ engine, one can leverage information about your location and its air quality to ensure customers have minimal risks to their health and wellbeing from the air quality in and around their homes.

It will be apparent to those of ordinary skill in the art that various changes and modifications may be made without deviating from the inventing concepts set from above. Thus, the scope of the present disclosure should not be limited to the structures described herein. Those having skill in the art will appreciate that many changes may be made to the details of the above-described embodiments and implementations without departing from the underlying principles thereof. Further, various modifications and alterations of the present invention will become apparent to those skilled in the art without departing from the spirit and scope of the invention. The scope of the present application should, therefore, be determined only by the following claims and equivalents thereof.

We claim:

1. A system for providing information regarding air quality, the system comprising:
    at least one of an air quality monitor at a first location in communication with a server; and an air filter at the first location or a second location including a sensor in communication with the server and capable of monitoring parameters relating to air flow;
    a processor associated with the server that executes instructions to perform operations comprising analyzing information to determine a relationship between the location and factors indicative of air quality; and
    providing a recommendation using the analyzed information for a user to at least one of:
        a) act to improve the air quality at either the first location or the second location;
        b) reward one or more residents or owners of the first location or the second location;
        c) penalize one or more residents or owners of the first location or the second location; and
        d) modify institutional behaviors and expectations at the first location or second location.

2. A method for distributing information regarding air quality, the method comprising:
    receiving information from at least one air quality monitor at a first location or a second location;
    receiving information from at least one sensor monitoring parameter relating to air flow through an air filter located at the first location;
    analyzing at least a portion of the received information to determine a relationship between the location and factors indicative of air quality;
    providing a recommendation using the analyzed information for a user to act to improve the air quality at either the first location or the second location.

* * * * *